United States Patent
Moszner et al.

(10) Patent No.: US 8,404,760 B2
(45) Date of Patent: Mar. 26, 2013

(54) FILLED DENTAL MATERIAL BASED ON POLYMERIZABLE DIHYDROXY-PHENYLALANINE DERIVATIVES

(75) Inventors: Norbert Moszner, Mauren (LI); Jörg Angermann, Sargans (CH); Urs Karl Fisher, Arbon (CH); Volker Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 126 days.

(21) Appl. No.: 12/889,481

(22) Filed: Sep. 24, 2010

(65) Prior Publication Data

US 2011/0118380 A1    May 19, 2011

(30) Foreign Application Priority Data

Nov. 19, 2009  (EP) .................................. 09014467

(51) Int. Cl.
  *A61K 6/083*  (2006.01)
(52) U.S. Cl. ...... 523/117; 523/115; 523/118; 433/228.1
(58) Field of Classification Search .................. 523/117, 523/115, 118; 433/228.1; 526/312
  See application file for complete search history.

(56) References Cited

U.S. PATENT DOCUMENTS

| | | | |
|---|---|---|---|
| 6,043,361 A | 3/2000 | Evans et al. | |
| 6,344,556 B1 | 2/2002 | Evans et al. | |
| 6,710,149 B2 * | 3/2004 | Moszner et al. | 526/278 |
| 7,585,901 B2 | 9/2009 | Moszner et al. | |
| 2006/0009550 A1 | 1/2006 | Messersmith et al. | |
| 2009/0163845 A1 * | 6/2009 | Meyer-Ingold | 602/54 |

FOREIGN PATENT DOCUMENTS

| | | |
|---|---|---|
| DE | 2658941 A1 | 7/1978 |
| DE | 19616183 A1 | 9/1997 |
| DE | 19643007 A1 | 4/1998 |
| DE | 19903177 C2 | 7/2000 |
| DE | 10082749 T1 | 2/2001 |
| WO | 2005118831 A2 | 12/2005 |
| WO | 2006045034 A1 | 4/2006 |

OTHER PUBLICATIONS

European Search Report of EP 09014467.6, Jun. 2010.
Lee et al., "Synthesis of 3,4-dihydroxphenylalanine (DOPA) containing monomers and their co-polymerization with PEG-diacrylate to form hydrogels," J. Biomater. Sci. Polymer Edn, 2004, vol. 15, No. 4, pp. 449-464.
Greene, "Protective Groups in Organic Synthesis," John Willey & Sons, 1980, pp. 1-2.
Hacksell, "Acta Pharmaceutica Suecica," Protective Goups in Organic Synthesis, 1986, vol. 23, No. 6, pp. 321-369.
Ooi et al., "Design of N-Spiro C2-Symmetric Chiral Quaternary Ammonium Bromides as Novel Chiral Phase-Transfer Catalysts: Synthesis and Application to Practical Asymmetric Synthesis of α-Amino Acids," JACS Articles, 2003, pp. 5139-5151.
Kolasa and Miller, "Synthesis of the Chromophore of Pseudobactin, a Fluroescent Siderophore from *Pseudomonas*," J. Org. Chem., 1990, vol. 55, pp. 4246-4255.
Suárez et al., "Stereospecific Syntheses of the Lignans: 2-S-(3,4-Dimethoxybenzyl)-3-R-(3,4,5-Trimethoxybenzyl) Butyrolactone, and its Positional Isomeric Lactone," Synthetic Communications, 2003, Vol. 23, No. 14, pp. 1991-2001.

* cited by examiner

*Primary Examiner* — Tae H Yoon
(74) *Attorney, Agent, or Firm* — Ann M. Knab; Thad McMurray

(57) ABSTRACT

Polymerizable dental material which contains (a) at least one radically polymerizable compound according to the general formula I Formula I

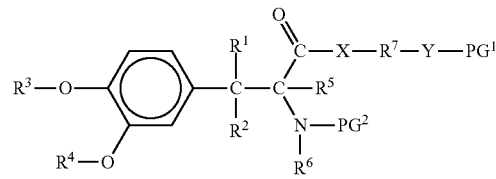

(b) initiators for radical polymerization; and (c) filler.

20 Claims, No Drawings

FILLED DENTAL MATERIAL BASED ON POLYMERIZABLE DIHYDROXY-PHENYLALANINE DERIVATIVES

This application claims the benefit of European Patent Application Serial No. 09014467.6, filed Nov. 19, 2009, which is hereby incorporated by reference in its entirety.

FIELD

The present invention relates to dental materials based on polymerizable dihydroxyphenylalanine derivatives which are suitable in particular as cements, composites and coatings.

BACKGROUND

DE 196 43 007 A1 discloses adhesion promoters and adhesives based on adhesive proteins which are coupled to polymerizable plastic monomers. A preferred adhesive protein is the Mytilus edulis foot protein isolated from the byssal threads of the common mussel. Adhesion promoters and adhesives are said to be suitable for dental applications.

WO 2006/045034 discloses self-etching dental primers which contain dihydroxyphenylalanine (DOPA) combined with dilute mineral acid and optionally olefinically unsaturated monomers, aldehydes and initiators for light-curing.

U.S. 2006/0009550 discloses the preparation of hydrogels by copolymerization of aqueous mixtures of poly(ethylene glycol)diacrylate and the radically polymerizable DOPA derivatives N-methacryloyl-3,4-dihydroxy-L-phenylalanine and N-(13-(N'-t-Boc-L-3',4'-dihydroxyphenylalaninamido)-4,7-10-trioxatridecanyl)-methacrylamide. The hydrogels are said to be suitable as surgical adhesives for medical or dental application and as carriers for delivering active ingredients to mucous membranes. It was found that DOPA derivatives exert an inhibiting effect on radical polymerization.

The synthesis of N-methacryloyl-3,4-dihydroxy-L-phenylalanine and N-(13-(N'-t-Boc-L-3',4'-dihydroxyphenylalaninamido)-4,7-10-trioxatridecanyl)-methacrylamide is described in Lee et al., J. Biomater. Sci. Polymer Edn. 15 (2004) 449-464.

L-DOPA is the immediate biological precursor of dopamine (3,4-dihydroxyphenethylamine), a drug for the therapeutic treatment of Parkinson's disease. It is known from DE 100 82 749 T1 that L-DOPA-containing copolymers of (meth)acrylic acid release the active ingredient L-DOPA in a controlled manner. This is necessarily associated with a degradation of the polymers.

Dental materials based on dihydroxyphenylalanine derivatives which are suitable as cements, composites and coatings are not known from the state of the art.

SUMMARY

An object of the invention is to provide dental materials which are suitable as cements, composites and coating materials which are characterized by a good adhesion to dentine and tooth enamel, which bond filler particles in securely and which are characterized by a good polymerizability.

The object is achieved according to the invention by dental materials, which
a) contain at least one radically polymerizable compound according to the general formula I

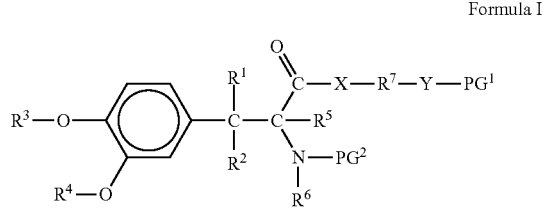

Formula I in which
$R^1$, $R^2$ independently of each other are each H or a $C_1$-$C_8$ alkyl residue,
$R^3$, $R^4$, $R^5$ independently of one another are each H or a $C_1$-$C_4$ alkyl residue,
$R^6$ is H, a linear or branched $C_1$-$C_{10}$ alkyl residue or a $C_1$-$C_{10}$ alkanoyl residue,
$R^7$ is a linear or branched $C_1$-$C_{15}$ alkylene residue or is dispensed with, wherein the chain of carbon atoms of the alkyl residue can be interrupted by O or S atoms, is preferably dispensed with or is a linear or branched $C_1$-$C_{15}$ alkylene residue,
X, Y independently of each other are each O or $NR^8$ or are dispensed with,
wherein $R^7$ can be dispensed with only if X and/or Y are also dispensed with, and
wherein $R^7$, X and Y can be dispensed with simultaneously only if $PG^1$=H,
$R^8$ is H or a $C_1$-$C_{10}$ alkyl residue,
$PG^1$, $PG^2$ independently of each other are each H or a radically polymerizable group, preferably a vinyl, allyl, (meth)acryl group, wherein the two residues $PG^1$ and $PG^2$ cannot simultaneously be H;
b) initiators for radical polymerization; and
c) filler.

The formula covers only those compounds that conform to the chemical valence theory.

The indication that a residue can be interrupted by a heteroatom such as O is to be understood such that the O atoms are inserted into the carbon chain of the residue, i.e. are bordered on both sides by carbon atoms. The number of heteroatoms is therefore at least 1 less than the number of carbon atoms, and the heteroatoms cannot be terminal.

Preferred meanings for the variables of Formula I are:
$R^1$, $R^2$ independently of each other each represent H or a $C_1$-$C_3$ alkyl residue, preferably H,
$R^3$, $R^4$ independently of each other each represent H or methyl, preferably H,
$R^5$ H or a $C_1$-$C_3$ alkyl residue, preferably H,
$R^6$ H, a linear or branched $C_1$-$C_2$ alkyl residue or a $C_2$ alkanoyl residue,
$R^7$ a linear $C_1$-$C_4$ alkylene residue or is dispensed with, wherein the chain of the carbon atoms of the alkyl residue can be interrupted by O atoms, preferably a $C_{1\text{-}4}$ alkyl residue,
X, Y independently of each other each represent O or $NR^8$ or are dispensed with,
$R^8$ H or $C_1$-$C_2$ alkyl residue,
$PG^1$, $PG^2$ independently of each other each represent H or a (meth)acryl group, wherein both residues cannot simultaneously be H.

Compounds according to Formula I in which $PG^2$ is a polymerizable group and $PG^1$ is H, and also compounds in which $PG^1$ and $PG^2$ are each a polymerizable group, are particularly preferred.

The preferred meanings of the variables can be chosen independently of each other. Compounds in which all variables have one of the preferred definitions are particularly preferred.

The materials according to the invention preferably contain 0.05 to 40 wt.-%, particularly preferably 1 to 30 wt.-% and quite particularly preferably 1 to 20 wt.-% of at least one compound according to Formula I. Unless stated otherwise, all percentages here relate to the total mass of the dental material.

It was surprisingly found that after curing the materials according to the invention have a high adhesion not only to collagen but also to dental hard tissue such as tooth enamel and dentine and to metallic substrates.

It was particularly surprising that the materials are well polymerizable and have good mechanical properties after curing. This was unexpected, as it was known from the state of the art that DOPA derivatives inhibit radical polymerization, which suggested particular problems with materials containing fillers, as in this case polymerization is additionally complicated by the filler. Surprisingly, however, the inhibiting effect of the DOPA was able to be counteracted by the addition of filler. The filler-containing materials according to the invention have a higher reactivity than corresponding unfilled materials and display a much higher polymerizability.

Moreover, it was known from the state of the art that DOPA-containing polymers can release DOPA, which on the one hand is disadvantageous for the mechanical stability of the polymers and on the other hand suggested the unwanted release of pharmaceutically active substances. However, the active ingredients according to the invention were stable even after storage in water and do not release unwanted components.

Polymerizable dihydroxyphenylalanine derivatives according to the general formula I are known from the state of the art and can be prepared by simple synthesis processes. For example, phenyl-D,L-alanine derivatives ($PG^1$, $PG^2$ and $R^5$, $R^6$=H; X and $R^7$ are dispensed with and Y=O) can be reacted with (meth)acrylic acid chloride ($PG^2$-Cl) to produce a corresponding polymerizable phenylalanine derivative:

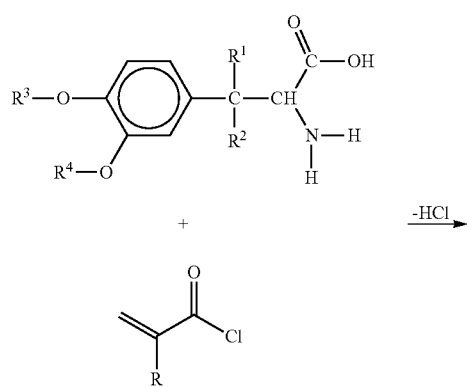

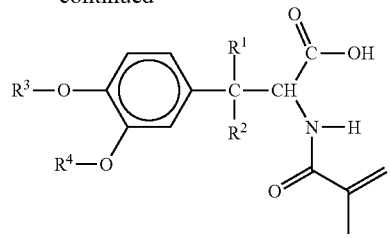

(R = H, CH₃)

SPECIFIC EXAMPLE

Synthesis of 3,4-dihydroxy-N-methacryloyl-DL-phenylalanine

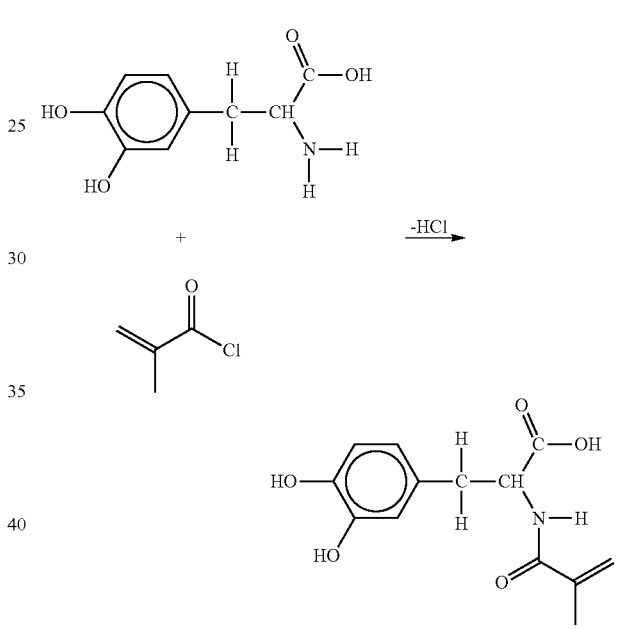

Phenyl-D,L-alanine derivatives with the substituents $R^1$, $R^2$, $R^3$, $R^4$, $R^5$ and $R^6$ can be prepared with known alkylation and acylation methods from organic chemistry and in consideration of the protective group technique (cf. T. W. Greene, Protective Groups in Organic Synthesis, J. Wiley & Sons, New York etc. (1980); Hacksell and Högberg, Protective Groups in Organic Synthesis, *Acta Pharm. Suec.* 23:323-369 (1986), which are hereby incorporated by reference in their entirety). DOPA derivatives substituted with $R^1$ or $R^2$ are accessible e.g. by using corresponding synthesis components during DOPA synthesis. Thus e.g. alkyl-substituted DOPA derivatives ($R^1$, $R^2$=alkyl) are accessible by reaction of α-terminal mono- or dialkyl-substituted benzyl bromides with glycine esters of benzophenone Schiff's bases analogously to Ooi et al., *J. Amer. Chem. Soc.* 125:5139 (2003), which is hereby incorporated by reference in its entirety). The alkylation of the phenolic OH groups ($R^3$ and $R^4$) can be carried out according to customary methods, for example by alkylation with the corresponding alkyl chlorides in the presence of KI analogously to Kolasa and Miller, *J. Org. Chem.* 55:4246 (1990), which is hereby incorporated by reference in its entirety. In this way, an alkylation of the amino group ($R^6$) can also be achieved. The alkylation of the phenolic OH groups ($R^3$ and $R^4$) is also possible with dialkyl sulphates analogously to Suarez et al., *Synth. Commun.* 23:1991 (1993), which is hereby incorporated by reference in its entirety. DOPA derivatives alkylated in α-position ($R^5$) are accessible for example via the hydrolysis of correspondingly substituted 2-imidazoline-5-ones analogous to DE 26 58 941 A1.

Preferred examples of polymerizable dihydroxyphenylalanine derivatives of general formula I are:

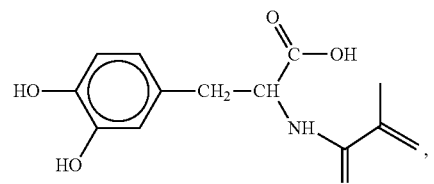

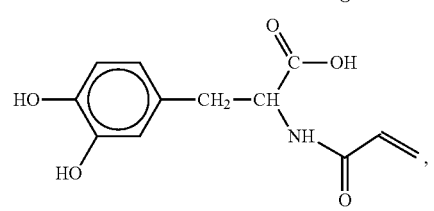

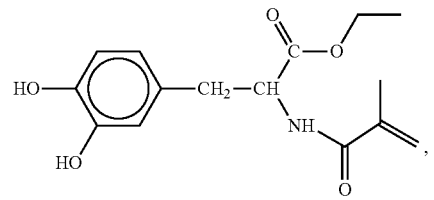

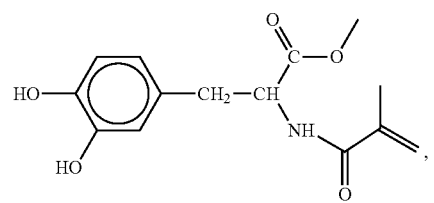

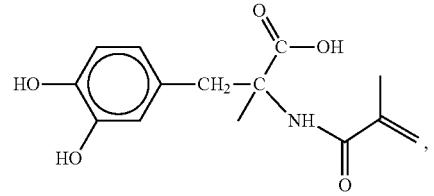

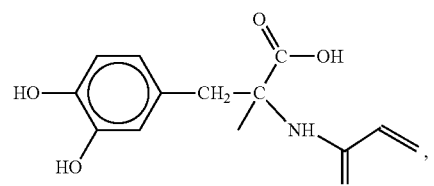

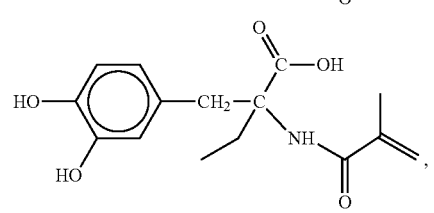

-continued

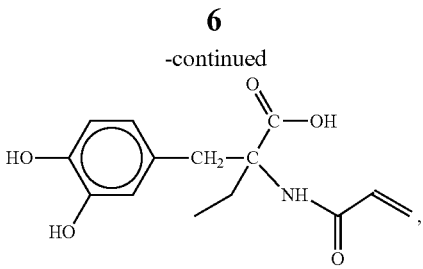

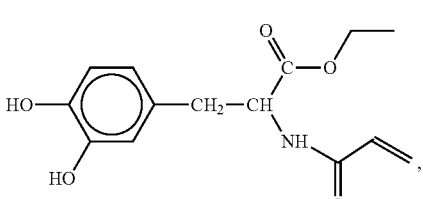

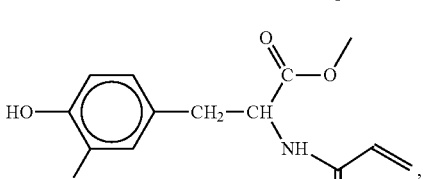

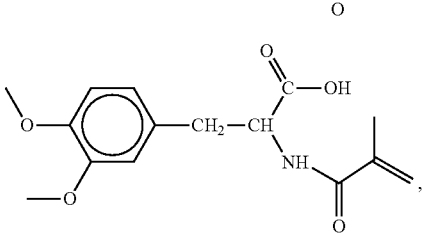

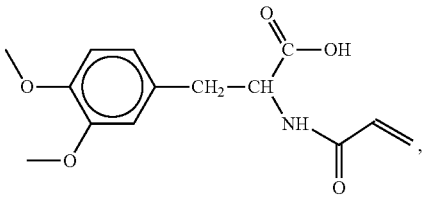

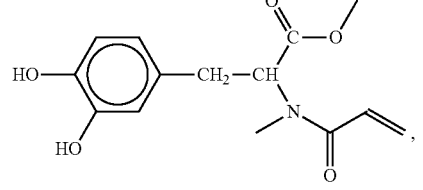

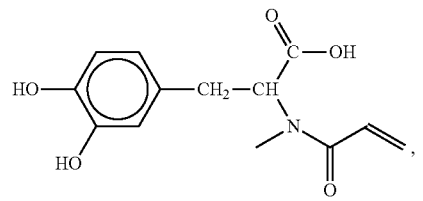

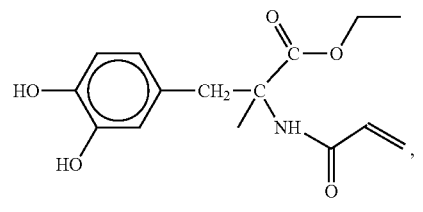

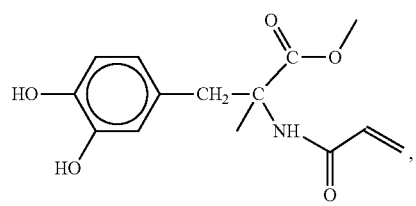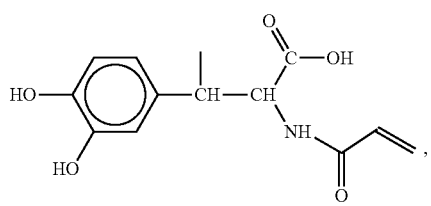

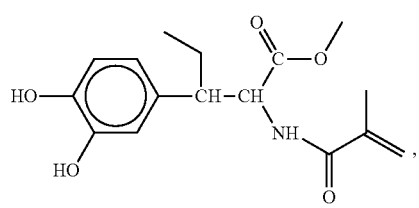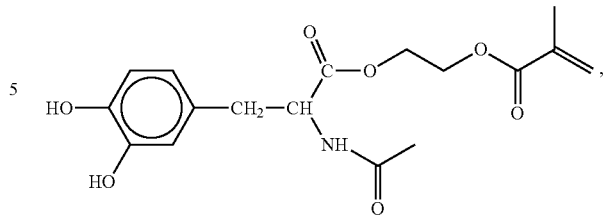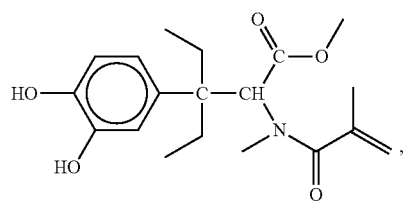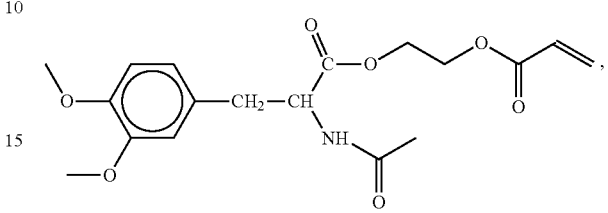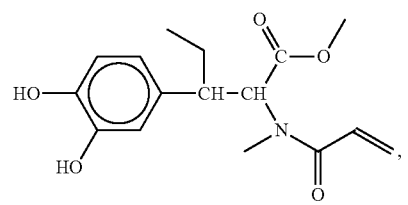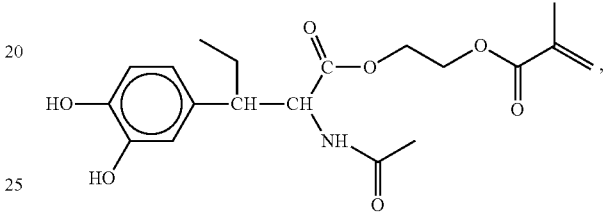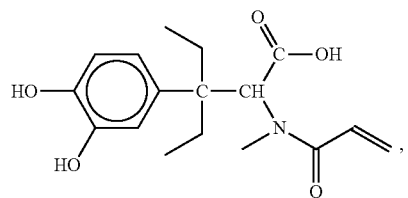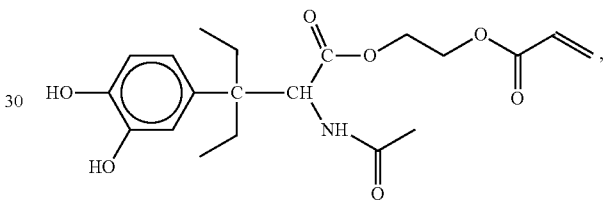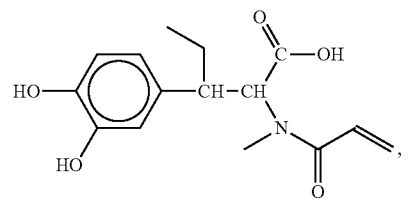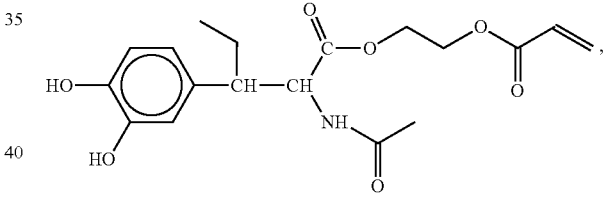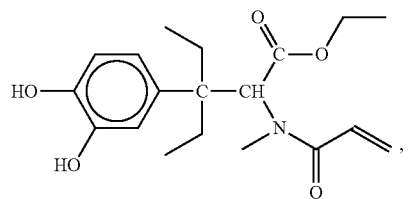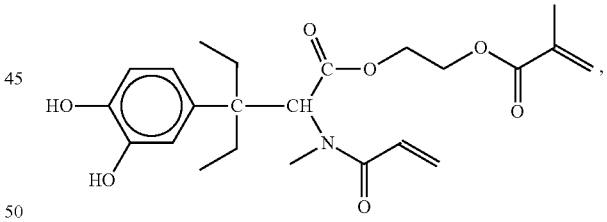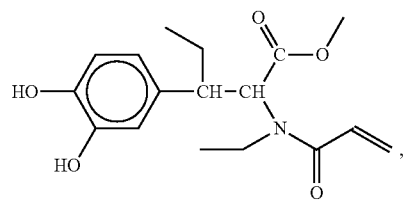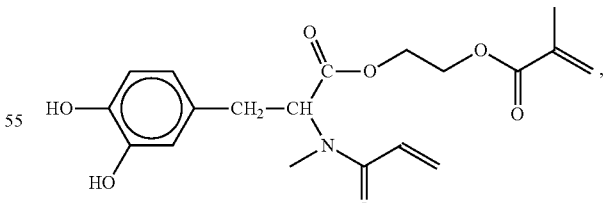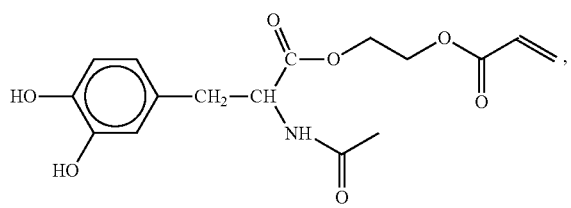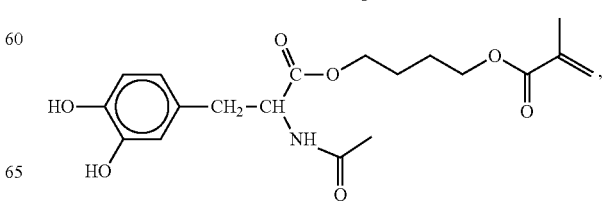

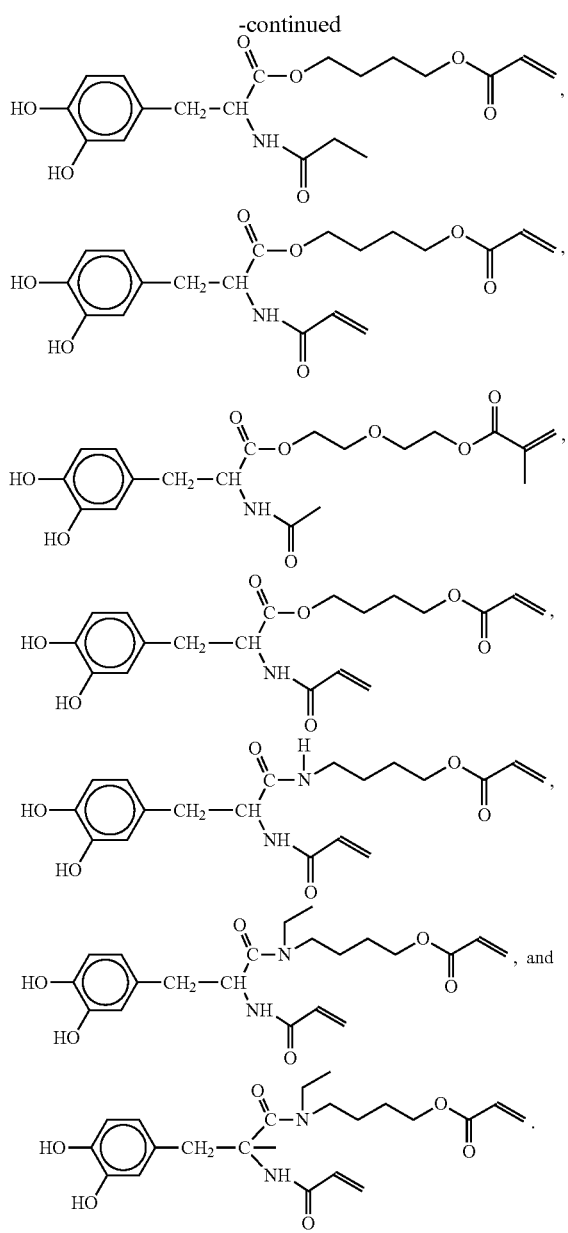

The polymerizable dihydroxyphenylalanine derivatives according to Formula I are well soluble in organic solvents such as acetone, acetonitrile or ethyl acetate and are thus particularly suitable as a constituent of hydrophobic composite matrices. They can therefore advantageously be combined with radically polymerizable monomers.

The dental materials according to the invention preferably contain mono- and/or polyfunctional (meth)acrylates as radically polymerizable monomers. By monofunctional monomers are meant monomers with one, by polyfunctional monomers monomers with more than one, radically polymerizable group. Preferred examples are methyl, ethyl, hydroxyethyl, butyl, benzyl, tetrahydrofurfuryl or isobornyl (meth)acrylate, bisphenol-A-di(meth)acrylate, bis-GMA (an addition product of methacrylic acid and bisphenol-A-diglycidyl ether), UDMA (an addition product of 2-hydroxyethyl methacrylate and 2,2,4-trimethylhexamethylene diisocyanate), di-, tri- or tetraethylene glycol di(meth)acrylate, trimethylolpropane tri(meth)acrylate, pentaerythritol tetra(meth)acrylate as well as glycerol dimethacrylate, 1,4-butanediol di(meth)acrylate, 1,10-decanediol di(meth)acrylate and 1,12-dodecanediol di(meth)acrylate.

Hydrolysis-resistant diluting and/or cross-linking monomers can preferably also be used as additional monomers. Preferred diluting monomers are hydrolysis-resistant mono (meth)acrylates, e.g. mesityl methacrylate, or 2-(alkoxymethyl)acrylic acids, e.g. 2-(ethoxymethyl)acrylic acid, 2-(hydroxymethyl)acrylic acid, N-mono- or N-disubstituted acrylamides, such as e.g. N-ethylacrylamide, N,N-dimethacrylamide, N-(2-hydroxyethyl)acrylamide, N-methyl-N-(2-hydroxyethyl)acrylamide, or N-monosubstituted methacrylamides, such as e.g. N-ethylmethacrylamide or N-(2-hydroxyethyl)methacrylamide and also in addition N-vinylpyrrolidone and allyl ether.

Examples of preferred hydrolysis-resistant cross-linking monomers are urethanes of 2-(hydroxymethyl)acrylic acid esters and diisocyanates such as 2,2,4-trimethylhexamethylene diisocyanate or isophorone diisocyanate, cross-linking pyrrolidones, such as e.g. 1,6-bis(3-vinyl-2-pyrrolidonyl)-hexane, or commercially available bisacrylamides, such as methylene or ethylene bisacrylamide, or bis(meth)acrylamides, such as e.g. N,N'-diethyl-1,3-bis(acrylamido)-propane, 1,3-bis(methacrylamido)-propane, 1,4-bis(acrylamido)-butane or 1,4-bis(acryloyl)-piperazine which can be synthesized from the corresponding diamines by reaction with (meth)acrylic acid chloride.

Furthermore, known low-shrinkage radically ring-opening polymerizable monomers, such as e.g. mono- or multifunctional vinyl cyclopropanes and bicyclic cyclopropane derivatives, preferably those described in DE 196 16 183 C2 and EP 03 022 855, or cyclic allyl sulphides, preferably those described in U.S. Pat. No. 6,043,361 or U.S. Pat. No. 6,344,556, can also be used as additional monomers. These monomers can also advantageously be used in combination with the di(meth)acrylate cross-linkers listed above.

Preferred ring-opening polymerizable monomers are vinyl cyclopropanes, in particular 1,1-di(ethoxycarbonyl)- or 1,1-di(methoxycarbonyl)-2-vinyl cyclopropane or the esters of 1-ethoxycarbonyl- or 1-methoxycarbonyl-2-vinyl cyclopropane carboxylic acid with ethylene glycol, 1,1,1-trimethylolpropane, 1,4-cyclohexanediol or resorcinol. Preferred bicyclic cyclopropane derivatives are 2-(bicyclo[3.1.0]hex-1-yl) acrylic acid methyl or ethyl esters or their disubstitution products in 3-position, such as (3,3-bis(ethoxycarbonyl)bicyclo[3.1.0]hex-1-yl)acrylic acid methyl or ethyl ester. Preferred cyclic allyl sulphides are the addition products of 2-(hydroxymethyl)-6-methylene-1,4-dithiepane or 7-hydroxy-3-methylene-1,5-dithiacyclooctane with 2,2,4-trimethylhexamethylene-1,6-diisocyanate or the asymmetric hexamethylene diisocyanate trimers (Desmodur® XP2410 from Bayer AG).

In addition, radically polymerizable polysiloxanes which can be prepared from suitable methacryl silanes, such as e.g. 3-(methacryloyloxy)propyltrimethoxysilane, can be used as additional monomers. The polysiloxanes described in DE 199 03 177 C2 are preferred.

Finally, mixtures of the monomers named above with radically polymerizable, acid group containing monomers, so-called adhesion monomers, can also be used as additional monomers. Preferred acid group containing monomers are polymerizable carboxylic acids such as maleic acid, acrylic acid, methacrylic acid, 2-(hydroxymethyl)acrylic acid, 4-(meth)acryloyloxyethyltrimellic acid anhydride, 10-methacryloyloxydecylmalonic acid, N-(2-hydroxy-3-methacryloyloxypropyl)-N-phenylglycine and 4-vinylbenzoic acid. Phosphonic acid monomers such as vinylphosphonic acid, 4-vinylphenylphosphonic acid, 4-vinylbenzylphosphonic acid, 2-methacryloyloxyethylphosphonic acid, 2-methacrylamidoethylphosphonic acid, 4-methacrylamido-4-methyl-pentyl-phosphonic acid, 2-[4-(dihydroxyphosphoryl)-2-oxa-butyl]-acrylic acid or 2-[4-(dihydroxyphosphoryl)-2-oxa-butyl]-acrylic acid ethyl- or -2,4,6-trimethylphenyl ester are further preferred. Acidic polymerizable phosphoric acid esters, such as 2-methacryloyloxypropyl mono- or dihydrogen phosphate, 2-methacryloyloxyethyl mono- or dihydrogen phosphate, 2-methacryloyloxyethylphenyl hydrogen phosphate, dipentaerythritol-pentamethacryloyloxyphosphate, 10-methacryloyloxyde-cyl-dihydrogen phosphate, phosphoric acid mono-(1-acryloyl-piperidine-4-yl)-ester, 6-(methacrylamido)hexyl dihydrogen phosphate and 1,3-bis-(N-acryloyl-N-propyl-amino)-propan-2-yl-dihydrogen phosphate are also preferred. Further preferred acid-group-containing monomers are polymerizable sulphonic acids such as vinylsulphonic acid, 4-vinylphenylsulphonic acid or 3-(methacrylamido)propylsulphonic acid.

The dental materials according to the invention preferably do not contain hydrophilic monomers, such as for example poly(ethylene glycol) di(meth)acrylates, which contribute to an increase in the water absorption of the materials and thus adversely affect their usability for dental purposes.

Dental materials which contain as additional radically polymerizable monomer at least one mono- and/or polyfunctional (meth)acrylate, bis-GMA, UDMA, trimethylolpropane trimethacrylate, glycerol dimethacrylate, 1,10-decanediol dimethacrylate, N,N'-diethyl-1,3-bis(acrylamido)-propane or a mixture thereof are particularly preferred.

Dental materials which contain as component (d) at least one further polymerizable monomer are preferred. Materials which contain 5 to 90 wt.-%, quite particularly preferably 20 to 80 wt.-% of one and/or several additional radically polymerizable mono- and/or polyfunctional diluting or cross-linking monomers are particularly preferred. Materials which also contain 0 to 50 wt.-%, quite particularly preferably 0 to 30 wt.-% of one and/or several radically polymerizable acid group containing monomers are further preferred. Materials which contain 5 to 80 wt.-% and quite particularly preferably 20 to 70 wt.-% of one or several polyfunctional monomers are particularly preferred. These percentages relate to the mass of the monomers in the materials.

Depending on the type of initiator used, the dental material can be hot-, cold- or light-polymerizable. Benzophenone, benzoin and derivatives thereof or α-diketones or derivatives thereof, such as 9,10-phenanthrenequinone, 1-phenyl-propan-1,2-dione, diacetyl or 4,4'-dichlorobenzil are used to initiate radical photopolymerization. Camphorquinone and 2,2-dimethoxy-2-phenyl-acetophenone are preferably used, and particularly preferably α-diketones combined with amines as reducing agents, such as e.g. 4-(dimethylamino)-benzoic acid esters, N,N-dimethylaminoethyl methacrylate, N,N-dimethyl-sym.-xylidine or triethanolamine. Norrish type I photoinitiators, above all acyl- or bisacylphosphine oxides, monoacyltrialkyl- or diacyldialkylgermanium compounds, such as e.g. benzoyltrimethylgermanium, dibenzoyldiethylgermanium or bis(4-methoxybenzoyl)diethylgermanium are also particularly preferred. Mixtures of different photo-initiators can also be used, such as e.g. dibenzoyldiethylgermanium combined with camphorquinone and 4-dimethylaminoethyl benzoate.

Benzopinacol and 2,2'-dialkylbenzopinacols are particularly suitable as initiators for hot-curing. Redox-initiator combinations, such as e.g. combinations of benzoyl peroxide with N,N-dimethyl-sym.-xylidine or N,N-dimethyl-p-toluidine, are used as initiators for a polymerization carried out at room temperature. In addition, redox systems consisting of peroxides and such reducing agents, such as e.g. ascorbic acid, barbiturates or sulphinic acids, are also particularly suitable.

Materials which contain a photoinitiator, in particular a photoinitiator based on camphorquinone/amine, a bisacylphosphine oxide, a diacyldialkylgermanium compound or a mixture thereof are preferred according to the invention.

The dental materials according to the invention preferably contain 0.01 to 10 wt.-%, preferably 0.1 to 3.0 wt.-% initiator and optionally an activator.

The compositions used according to the invention furthermore contain organic or inorganic filler particles to improve the mechanical properties or to adjust the viscosity. The filler particles preferably have an average particle size [determined by transmission (10-80 nm) or scanning electron microscopy (50 nm to 5 µm) or laser diffraction (0.1 to 100 µm)] of 10 nm to 50 µm, particularly preferably 10 nm to 30 µm and quite particularly preferably 10 nm to 5 µm.

Preferred inorganic particulate fillers are amorphous spherical materials based on oxides, such as $ZrO_2$ and $TiO_2$ or mixed oxides of $SiO_2$, $ZrO_2$ and/or $TiO_2$ with an average particle size from 10 nm to 1 µm, nanoparticulate or microfine fillers such as pyrogenic silicic acid or precipitation silicic acid with an average particle size from 10 nm to 500 nm and also mini fillers such as quartz, ceramic, glass ceramic or glass powder with an average particle size from 0.1 to 5 µm, preferably 0.2 to 3 µm and quite particularly preferably 0.4 to 1.5 µm as well as X-ray-opaque fillers such as ytterbium trifluoride or nanoparticulate tantalum(V) oxide or barium sulphate with an average particle size from 10 nm to 500 nm.

The dental materials according to the invention preferably contain 1 to 90 wt.-%, preferably 1 to 85 wt.-% and quite preferably 1 to 20 wt.-% or 20 to 85 wt.-% filler, wherein the filler content depends on the desired intended use of the materials. The fillers contribute substantially to the curing of the materials.

The compositions used according to the invention can optionally contain further additives, in particular solvents, such as acetone, ethyl acetate and mixtures thereof, as well as stabilizers, flavourings, dyes, microbiocidal active ingredients, fluoride-ion-releasing additives, optical brighteners, plasticizers or UV absorbers. The dental materials according to the invention preferably contain no water, i.e. 0.5 wt.-% water at most.

According to a further preferred embodiment, the materials according to the invention contain boric acid, preferably in a quantity from 0 to 2.0 mol equivalent relative to the compound according to Formula I, particularly preferably 0 to 1.0 mol equivalent. It was found that boric acid, in particular in the case of $R^3=R^4=H$, reduces the inhibiting effect of DOPA derivatives on radical polymerization. Therefore when boric acid is used the addition of filler can be dispensed with, wherein materials which contain filler and boric acid are preferred.

Compositions which contain as component (e) 0 to 95 wt.-%, particularly preferably 0 to 70 wt.-% and quite particularly preferably 5 to 50 wt.-% non-aqueous solvent are particularly suitable according to the invention.

The dental materials according to the invention preferably contain:
 a) 0.05 to 40.0 wt. %, preferably 1 to 30 wt. % and particularly preferably 1 to 20 wt. % of at least one compound according to Formula I;
 b) 0.01 to 10 wt. %, preferably 0.1 to 3.0 wt. % initiator;

c) 1 to 85 wt. %, preferably 1 to 20 wt. % (for use as coating material) or 20 to 85 wt. % (for use as cement or composite) filler;
d) 0 to 90 wt. %, preferably 0 to 80% wt. % and particularly preferably 5 to 80 wt. % of at least one additional monomer;
e) 0 to 95 wt. %, preferably 0 to 70 wt. % and particularly preferably 5 to 50 wt. % solvent.

The dental materials according to the invention are particularly suitable as cements, composite materials, filling materials, adhesives and as coating materials.

The invention is explained in more detail below by means of examples.

EMBODIMENT EXAMPLES

Example 1

Synthesis of Polymerizable 3,4-Dihydroxy-DL-Phenylalanines (DL-DOPA)

General Procedure for the N-acylation of DL-DOPA:
A mixture of 19.72 g (0.10 mol) DL-DOPA, 64.56 g (0.40 mol) hexamethyldisilazane and 4.00 ml trimethylchlorosilane was stirred for 3 h at 120° C. bath temperature. Volatile constituents were then removed at 70° C./20 mbar. 50 ml xylene was added to the residue and the mixture re-concentrated (70° C./20 mbar). The thus-obtained intermediate stage was dissolved in 200 ml methylene chloride, a solution of 0.10 mol acid chloride in 20 ml methylene chloride added to it at −70° C. and the mixture stirred accompanied by slow heating to room temperature for 2 d. After concentration in vacuum (40° C./600 mbar) 500 ml tert-butanol and 100 ml water were added to the residue, the mixture stirred for 30 min at room temperature, dried with sodium sulphate, filtered and the solvent distilled off (40° C./20 mbar). For purification, the raw product was heated under reflux in 250 ml ethyl acetate for 1 h and filtered off from the undissolved material. The clear, yellow filtrate was desolventized (40° C./180 mbar) and then dried at 0.1 mbar to a constant weight.

a) 3,4-dihydroxy-N-methacryloyl-DL-phenylalanine (MADOPA)

MADOPA was obtained using methacrylic acid chloride. Yield: 14.8 g (56%), yellowish solid (m.p.: 63-65° C.). Purity (HPLC): 96.16%

$^1$H-NMR (400 MHz, DMSO-$d_6$): δ=1.79 (s, 3H, $CH_3$), 2.76-2.92 (m, 2H, $CH_2$), 4.30-4.36 (m, 1H, NCH), 5.31, 5.62 (2 s, each 1H, =$CH_2$), 6.47, 6.58, 6.60-6.61 (dd, J=8 Hz, 2 Hz, 1H; s, 1H; m, 1H, =CH—), 7.93 (d, J=8 Hz, 1H, NH), 8.71 (br. s, 2H, OH), 12.5 (br. s, 1H, COOH).

$^{13}$C-NMR (100 MHz, DMSO-$d_6$): δ=18.5 ($CH_3$), 35.7 ($CH_2$), 54.1 (NCH), 115.2, 116.4, 119.8 (=$CH_{aromatic}$), 119.5 (C=$CH_2$), 128.7, (=$C_{aromatic}$), 139.4 (C=$CH_2$), 143.7, 144.8 (HO—C=), 167.5 (CONH), 173.2 (COOH).

IR (diamond ATR): ν=3202 (br, m, N—H, O—H), 2933 (m, $CH_2$, $CH_3$), 1717 (s, C=$O_{acid}$), 1652 (s, C=$O_{amide}$), 1604 (s, C=C), 1532 (s, N—H), 1444 (s, aromatic), 1422 (s, $CH_2$, $CH_3$), 1372 (m, $CH_3$), 1194 (s, C—OH), 1116 (s, C—N), 873 cm$^{-1}$ (s, =CH).

b) N-acryloyl-3,4-dihydroxy-DL-phenylalanine (ADOPA)

ADOPA was obtained using acrylic acid chloride. Yield: 14.8 g (56%), yellowish solid (m.p.: 143-145° C.). Purity (HPLC): 95.84%.

$^1$H-NMR (400 MHz, DMSO-$d_6$): δ=2.69-2.92 (m, 2H, $CH_2$), 4.39-4.44 (m, 1H, NCH), 5.57-5.60, 6.04-6.08, 6.26-6.32 (3 m, each 1H, HC=$CH_2$), 6.47, 6.61 (d, J=8 Hz, 1H; s, 2H, =$CH_{aromatic}$), 8.35 (d, J=8 Hz, 1H, NH), 8.70, 8.74 (2 br. s, each 1H, OH), 12.7 (br. s, 1H, COOH).

$^{13}$C-NMR (100 MHz, DMSO-$d_6$): δ=36.2 ($CH_2$), 53.8 (NCH), 115.3, 116.3, 119.7 (=$CH_{aromatic}$), 125.6 (HC=$CH_2$), 128.2, (=$C_{aromatic}$), 131.3 (HC=$CH_2$), 143.8, 144.9 (HO—C=), 164.4 (CONH), 173.0 (COOH).

IR (diamond ATR): ν=3300 (br, m, N—H, O—H), 2920 (m, $CH_2$), 1717 (s, C=$O_{acid}$), 1653 (s, C=$O_{amide}$), 1601 (s, C=C), 1516 (ss, N—H), 1444 (s, aromatic), 1414 (s, $CH_2$), 1191 (s, C—OH), 1114 (s, C—N), 969 (s, =CH), 871 cm$^{-1}$ (s, =CH).

Example 2

Radical Homopolymerization of MADOPA in Solution

The monomer MADOPA (2.0 mol/l) was polymerized in DMF with 2,2'-azobisisobutyronitrile (AIBN, 2.0 mol %) at 65° C. After 5 h the polymerization was stopped and the polymerisate precipitated out of ten times the quantity of diethyl ether, filtered off and dried to constant weight in fine vacuum at 50° C. A white polymer was obtained in virtually quantitative yield. The polymer structure was able to be confirmed by means of $^1$H-NMR spectroscopy.

NMR spectroscopy data for poly(MADOPA):

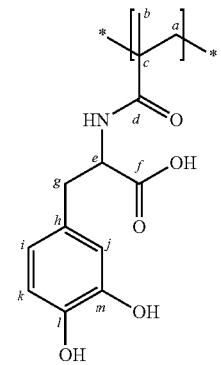

$^1$H-NMR (400 MHz, MeOD, δ in ppm): 0.88 ($H_a$, $H_b$, 5H), 2.6-3.1 ($H_g$, 2H), 4.57 ($H_e$, 1H), 6.75 ($H_i$, $H_j$, $H_k$, 3H), 8.0 ($H_{NH}$, 1H)

$^{13}$C-NMR (100 MHz, MeOD, δ in ppm): 19.4 $C_b$, 37.9 $C_g$, 46.8 $C_c$, 48.9 $C_e$, 56.2 $C_a$, 117.7 $C_{j/k}$, 122.3 $C_i$, 129.9 $C_h$, 145.2 $C_l$, 146.2 $C_m$, 175.1 $C_f$, 178.9 $C_d$ Example 3

Radical Copolymerization of ADOPA with MMA in Solution

The monomer ADOPA (0.2 mol/l) and methyl methacrylate (MMA) (1.8 mol/l) were polymerized in DMF with 2,2'-azobisisobutyronitrile (AIBN, 2.0 mol %) at 65° C. After 5 h the polymerization was stopped and the polymerisate precipitated out of ten times the quantity of methanol, filtered off and dried to constant weight in fine vacuum. A white polymer was obtained in virtually quantitative yield. The polymer structure was able to be confirmed by means of ¹H-NMR spectroscopy. A copolymer structure with 18 mol % ADOPA units resulted.

Example 4

Preparation of Composite Cements Based on MADOPA

According to Table 1 given below, composite fixing cements based on a dimethacrylate mixture were prepared with the polymerizable DOPA derivative MADOPA (cement A) and the monofunctional benzyl methacrylate (cement B, comparison example) and also bis-(4-methoxybenzoyl)diethylgermanium as photoinitiator by means of an "Exakt" roll mill (Exakt Apparatebau, Norderstedt). Testpieces (rods with a length of 25 mm and a square cross-section of 2 mm×2 mm) were prepared from the materials which were irradiated twice for 3 minutes with a dental light source (Spectramat®, Ivoclar Vivadent AG) and cured. The bending strength and the bending E modulus were determined according to ISO standard ISO 4049 (Dentistry—Polymer-based filling, restorative and luting materials). The results are summarized in Table 2.

The example shows that filled DOPA-monomer-containing formulations lead to composite cements with good mechanical properties, while analogous unfilled resins do not produce usable materials.

TABLE 1

Composition of the composite cements

| Component | Cement A [wt.-%] | Resin A*) [wt.-%] | Cement B*) [wt.-%] |
|---|---|---|---|
| Bis(4-methoxybenzoyl)diethylgermanium | 0.58 | 1.45 | 0.58 |
| UDMA[1)] | 27.64 | 69.10 | 27.64 |
| Triethylene glycol dimethacrylate | 7.81 | 19.53 | 7.81 |
| MADOPA (Ex. 1a) | 3.90 | 9.92 | — |
| Benzyl methacrylate | — | — | 3.90 |
| Pyrogenic silicic acid[2)] | 41.34 | — | 41.34 |
| Ytterbium trifluoride (Rhone-Poulenc) | 18.73 | — | 18.73 |

*)Comparison
[1)]Addition product of 2 mol 2-hydroxyethyl methacrylate and 1 mol 2,2,4-trimethylhexamethylene diisocyanate
[2)]Aerosil OX-50 (Degussa)

TABLE 2

Mechanical properties of the composite cements

| Property | Cement A | Resin A*) | Cement B*) |
|---|---|---|---|
| Bending strength (MPa) after 24 h WI[1)] | 114 | 32 | 109 |
| Elastic modulus (MPa) after 24 h WI[1)] | 5280 | 600 | 5200 |

*)Comparison
[1)]WI = water immersion of the testpieces at 37° C.

Example 5

Preparation of a Composite Based on MADOPA

Dental composites with the composition given in Table 3 were prepared using a Linden kneader. The mechanical properties were examined analogously to Example 4 and are summarized in Table 4.

TABLE 3

Composition of the composites

| Component | Composite C [wt-%] | Composite D*) [wt.-%] |
|---|---|---|
| Bis(4-methoxybenzoyl)diethylgermanium | 0.22 | 0.22 |
| UDMA[1)] | 6.72 | 6.72 |
| Triethylene glycol dimethacrylate | 1.77 | 6.72 |
| MADOPA | 1.81 | — |
| Benzyl methacrylate | — | 1.81 |
| Ytterbium trifluoride (Rhone-Poulenc) | 14.89 | 14.89 |
| Spherosil, silanized (Tokoyama Soda)[2)] | 14.39 | 14.39 |
| Glass filler GM27884 (Schott)[3)] | 51.61 | 51.61 |
| Aerosil OX-50 (Degussa) | 1.00 | 1.00 |

*)Comparison
[1)]Addition product of 2 mol 2-hydroxyethyl methacrylate and 1 mol 2,2,4-trimethylhexamethylene diisocyanate
[2)]$SiO_2$—$ZrO_2$ mixed oxide (average primary particle size: 250 nm)
[3)]Silanized Ba—Al-boron silicate glass filler with an average particle size of 1.5 μm

TABLE 4

Mechanical properties of the composites

| Property | Composite C | Composite D*) |
|---|---|---|
| Bending strength (MPa) after 24 h WI[1)] | 158 | 195 |
| Elastic modulus (MPa) after 24 h WI[1)] | 15000 | 16200 |

*)Comparison
[1)]WI = water immersion of the testpieces at 37° C.

It should be mentioned that any references, including patents, patent applications and published articles that are cited herein are incorporated by reference in their entirety. Any word used herein in plural form may also include singular forms of the word and any word used in singular form herein may also include plural forms of the word.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

What is claimed:

1. Polymerizable dental material, which comprises
   a) at least one radically polymerizable compound according to the general formula I

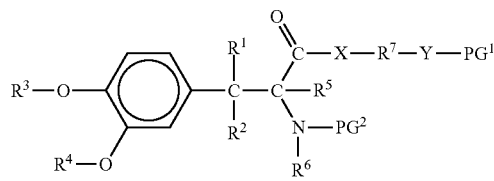

Formula I in which
$R^1$, $R^2$ are each H,
$R^3$, $R^4$, $R^5$ are each H,
$R^6$ is H, a linear or branched $C_1$-$C_2$ alkyl residue or a $C_2$ alkanoyl residue,
$R^7$ is a linear $C_1$-$C_4$ alkylene residue,
X, Y independently of each other are each O or $NR^8$ or are dispensed with,
$R^8$ is H or a $C_1$-$C_2$ alkyl residue,
$PG^1$, $PG^2$ independently of each other are each H or a (methy)acryl group, wherein both residues $PG^1$ and $PG^2$ cannot simultaneously be H;

b) an initiator for radical polymerization; and
c) a filler.

2. Dental material according to claim 1, which further comprises at least one of
   d) an additional polymerizable monomer and
   e) a solvent.

3. Dental material according to claim 1, which comprises
   a) 0.05 to 40 wt.-% of at least one compound according to Formula I;
   b) 0.01 to 10 wt.-% initiator;
   c) 1 to 85 wt.-% filler;
   d) 0 to 90 wt.-% of at least one additional monomer; and
   e) 0 to 95 wt.-% solvent.

4. Dental material according to claim 2, wherein the additional polymerizable monomer comprises at least one mono- and/or polyfunctional (meth)acrylate.

5. Dental material according to claim 2, which is free of hydrophilic monomers.

6. Dental material according to claim 1, wherein the filler has an average particle size from 10 nm to 50 µm.

7. Dental material according to claim 1, wherein the filler comprises amorphous spherical materials based on oxides or mixed oxides with an average particle size from 10 nm to 1 µm, and/or nanoparticulate or microfine fillers with an average particle size from 10 nm to 500 nm, and/or mini fillers with an average particle size from 0.1 to 5 µm, and/or X-ray-opaque fillers with an average particle size from 10 nm to 500 nm.

8. Dental material according to claim 1, which contains 0.5 wt.-% water at most.

9. Dental material according to claim 1, which contains boric acid in a quantity from 0 to 2.0 mol equivalent relative to the compound according to Formula I.

10. Dental material according to claim 3 for use as a coating material, which comprises
    a) 1 to 30 wt.-% of at least one compound according to Formula I;
    b) 0.1 to 3.0 wt.-% initiator;
    c) 1 to 20 wt.-% filler;
    d) 0 to 80 wt.-% of at least one additional monomer; and
    e) 0 to 70 wt.-% solvent.

11. Dental material according to claim 3 for use as a cement or composite, which comprises
    a) 1 to 30 wt.-% of at least one compound according to Formula I;
    b) 0.1 to 3.0 wt.-% initiator;
    c) 20 to 85 wt.-% filler;
    d) 0 to 80 wt.-% of at least one additional monomer; and
    e) 0 to 70 wt.-% solvent.

12. Dental material according to claim 6, wherein the filler comprises an average particle size from 10 nm to 30 µm.

13. Dental material according to claim 6, wherein the filler comprises an average particle size from 10 nm to 5 µm.

14. Dental material according to claim 9, wherein the boric acid quantity is 0 to 1.0 mol equivalent.

15. Dental material according to claim 2, wherein the additional polymerizable monomer comprises at least one N-monosubstituted acrylamide and/or at least one N-disubstituted acrylamide and/or at least one N-monosubstituted methacrylamide.

16. A dental cement, composite material, filling material, adhesive or coating material, comprising the dental material of claim 1.

17. Dental material according to claim 3, which comprises
    d) 5 to 90 wt.-% of at least one additional monomer.

18. Dental material according to claim 17, which comprises
    d) 5 to 80 wt.-% of at least one additional monomer.

19. Dental material according to claim 3, which comprises
    e) 0 to 70 wt.-% solvent.

20. Dental material according to claim 19, which comprises
    e) 0 to 50 wt.-% solvent.

* * * * *

UNITED STATES PATENT AND TRADEMARK OFFICE
CERTIFICATE OF CORRECTION

PATENT NO. : 8,404,760 B2  
APPLICATION NO. : 12/889481  
DATED : March 26, 2013  
INVENTOR(S) : Moszner et al.

Page 1 of 1

It is certified that error appears in the above-identified patent and that said Letters Patent is hereby corrected as shown below:

On the Title page, item (75) should read:

--(75) Inventors: Norbert Moszner, Mauren (LI); Jörg Angermann, Sargans (CH); Urs Karl Fischer, Arbon (CH); Volker Rheinberger, Vaduz (LI)--

Signed and Sealed this  
Tenth Day of September, 2013

Teresa Stanek Rea  
*Acting Director of the United States Patent and Trademark Office*